United States Patent [19]

Horstmann et al.

[11] 4,369,324
[45] Jan. 18, 1983

[54] PROCESS FOR THE PREPARATION OF 2-AMINO-6-NITROBENZOTHIAZOLE

[75] Inventors: Walter Horstmann, Bergisch Gladbach, Fed. Rep. of Germany; Richard Sommer, Summerville, S.C.; Hans Trautwein, Odenthal-Voiswinkel; Gerhard Wolfrum, Leverkusen, both of Fed. Rep. of Germany

[73] Assignee: Bayer Aktiengesellschaft, Leverkusen, Fed. Rep. of Germany

[21] Appl. No.: 256,636

[22] Filed: Apr. 23, 1981

[30] Foreign Application Priority Data

May 10, 1980 [DE] Fed. Rep. of Germany ....... 3018028

[51] Int. Cl.$^3$ ........................................... C07D 277/82
[52] U.S. Cl. ................................... 548/164; 548/163
[58] Field of Search ......................................... 548/164

[56] References Cited

U.S. PATENT DOCUMENTS 3,057,848  10/1962  Dehn et al. .................. 548/164

*Primary Examiner*—Donald G. Daus
*Assistant Examiner*—D. B. Springer
*Attorney, Agent, or Firm*—Sprung, Horn, Kramer & Woods

[57] ABSTRACT

2-Amino-6-nitrobenzothiazole is obtained with a high selectivity if, instead of unprotected 2-aminobenzothiazole, acylation products thereof are nitrated and the acyl groups are then split off. 2-Amino-6-nitrobenzothiazole is an important intermediate product for the preparation of valuable azo dyestuffs.

4 Claims, No Drawings

PROCESS FOR THE PREPARATION OF 2-AMINO-6-NITROBENZOTHIAZOLE

The present invention relates to a process for the preparation of 2-amino-6-nitrobenzothiazole.

It is already known that the title compound can be prepared by direct nitration of 2-aminobenzothiazole (compare J. Chem. Soc. 1930, 2203). However, this process has the disadvantage that it gives an isomer mixture which contains the desired 6-nitro compound only to the extent of about 20%.

It has now been found, surprisingly, that the 6-nitro compound is obtained with a high selectivity if, instead of 2-aminobenzothiazole as such, acylation products thereof are nitrated and the acyl groups are then split off.

Suitable 2-acylaminobenzothiazoles are, in particular, those of the formula

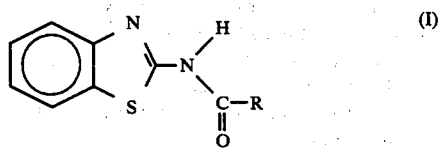

in which

R denotes hydrogen, alkyl, alkoxy, trifluoromethyl or carboxyalkyl.

Possible alkyl, alkoxy and carboxyalkyl radicals are, in particular, those with 1 to 4 carbon atoms. The formyl radical and the acetyl radical are preferred.

The 2-acylaminobenzothiazoles used as the starting material are known, or they can easily be obtained by known processes, by reacting 2-aminobenzothiazole with corresponding acid chlorides or anhydrides, chlorocarbonic acid esters or oxalic acid esters (compare Annalen der Chemie 212, 326 (1882); U.S. Patent Specification 2,833,689; and German Offenlegungsschrift 2,656,468).

2-Aminobenzothiazole is in turn most easily obtained by the action of hydroxylamine on benzothiazole (compare Annalen der Chemie 419, 65 (1919)), which is a waste product of the preparation of 2-mercaptobenzothiazole on a large industrial scale.

The use of this undesired by-product, for which there has hitherto been no satisfactory possibility of utilisation, in the preparation of 2-amino-6-nitrobenzothiazole is to be regarded as another important advantage of the process according to the invention.

The acyl compounds are nitrated by methods which are known per se. It is expedient to follow a procedure in which the acyl compound is dissolved in 2 to 6 times the amount by weight of sulphuric acid and then nitrated with a mixture of nitric acid and sulphuric acid, preferably at 0° to 50° C. The nitric acid content of the mixed acid should be 5 to 60% by weight, and the molar ratio of acylaminobenzothiazole to nitric acid should be 1.0:1.0 to 1.5.

The nitration of the 2-acylaminobenzothiazoles can also be carried out with nitric acid by itself, in which case the weight ratio of the component can be 1:2 to 1:10.

The nitration mixture is worked up in the customary manner, for example by discharging onto ice.

The acyl group is also split off in a manner which is known per se, by saponification with dilute mineral acids, alkali metal hydroxide solutions or ammonia solution in aqueous or aqueous-alcoholic solution or suspension, at elevated temperatures and if appropriate with the application of pressure. Temperatures of 20° to 150° C., preferably 40° to 100° C., and pressures up to 50 bars have proved advantageous.

2-Amino-6-nitrobenzothiazole is obtained in two crystal modifications, depending on the choice of the experimental conditions. The modification designated A consists of needle-shaped, light-yellow crystals with a low bulk density, whilst modification B consists of coarse, yellow-brown coloured crystals with a relatively high density. The two modifications differ roentgenographically with respect to their Debye-Scherrer diagrams:

| α-values | Intensity (estimated) |
|---|---|
| Modification A | |
| 3.20 A | 100 |
| 6.13 A | 40 |
| 7.94 A | 40 |
| 3.75 A | 20 |
| Modification B | |
| 3.53 A | 100 |
| 5.22 A | 60 |
| 3.05 A | 40 |
| 4.67 A | 20 |

2-Amino-6-nitrobenzothiazole is an important intermediate product for the preparation of azo dyestuffs (compare Japanese Patent Publication 13389/69).

The 2-amino-6-nitrobenzothiazole obtained by the process according to the invention can be used without further purification for the preparation of dyestuffs.

EXAMPLE 1

192 g (1.0 mol) of 2-acetylaminobenzothiazole (Annalen 212, 326 (1882)) are introduced into 490 g of sulphuric acid monohydrate at 20° to 30° C. The mixture is cooled to 5° to 10° C. and nitration is carried out in this temperature range with 200 g of mixed acid containing 31.5% of nitric acid. After dropwise addition of the mixed acid, the mixture is stirred at 10° to 15° C. for 2 hours and is then discharged onto 1,000 g of ice. The precipitate is isolated and washed with about 5 l of water in portions. 1,100 g of water-moist 2-acetylamino-6-nitrobenzothiazole are obtained.

The moist presscake is suspended in 1,650 ml of methanol. The suspension is heated to 60° C. and adjusted to a pH value of 10.5 with concentrated sodium hydroxide solution. About 60 ml of sodium hydroxide solution are consumed in the course of 5 hours, in order to maintain this pH value. The mixture is now cooled to 20° C. and the 2-amino-6-nitrobenzothiazole (modification B) which has crystallised out is isolated and washed with 200 ml of methanol, and then with water until free from alkali. After drying the product at 50° C. in a vacuum drying cabinet, a yield of 171 g, with a melting point of 248° to 252° C., is obtained. The 2-amino-5-nitrobenzothiazole content is 0.3%. 2-Amino-6-nitrobenzothiazole of this quality can be used directly, without further purification operations, for the preparation of dyestuffs.

EXAMPLE 2 (COMPARISON EXAMPLE)

In analogy to Hunter and Jones (J.Chem.Soc. 1930, 2203) 15.0 g (0.1 mol) of 2-amino-benzthiazole are introduced into 90 ml of nitric acid (density: 1.5) at 0° to 5° C. in the course of 15 minutes.

The reaction mixture is subsequently stirred for one hour, discharged onto 900 ml of ice-water and adjusted to a pH value of 8 with about 170 ml of 25% strength ammonia solution. The precipitate is isolated, washed with water until neutral and dried in vacuo at 50° C. 19.2 g of a product which consists of 2-amino-5-nitrobenzothiazole to the extent of 70-80%, 2-amino-6-nitrobenzothiazole to the extent of 15-20% and other mononitro and dinitro isomers to the extent of 5-10% are obtained. This method is unsuitable for the industrial preparation of 2-amino-6-nitro-benzothiazole.

EXAMPLE 3

96 g (0.5 mol) of 2-acetylaminobenzothiazole are introduced into 300 g of 94% strength nitric acid at 0° to 5° C. The mixture is subsequently stirred for 3 hours without external cooling. During this procedure, the temperature rises to 28° C. The batch is discharged onto 600 g of an ice/water mixture and the solid is filtered off and rinsed with 2 l of water in portions. 459 g of a paste consisting of 2-acetylamino-6-nitrobenzothiazole are obtained. This paste is suspended in 900 ml of methanol and saponification is carried out as described in Example 1. The yield is 67 g of 2-amino-6-nitrobenzothiazole of melting point 246° to 249° C. The 2-amino-5-nitrobenzothiazole content is less than 0.1%. The product can be employed, without further purification, for the preparation of dyestuffs.

EXAMPLE 4

19 g (0.09 mol) of benzothiazol-2-yl-carbamic acid ethyl ester are nitrated as described in Example 1. The resulting water-moist paste of 6-nitro-benzothiazol-2-yl-carbamic acid ethyl ester is saponified at pH 10 to 12 and the mixture is worked up, as described in Example 1. 9.8 g of 2-amino-6-nitrobenzothiazole of melting point 249° to 252° C. are obtained. The content of isomeric nitro compounds is less than 1%.

EXAMPLE 5

35.6 g of 2-benzothiazolyl-formamide (prepared in accordance with the statements of C. W. Huffmann, J.Org. Chem. 23, 727-729 [1958]) are nitrated and the mixture is worked up, as described in Example 1 for 2-acetylaminobenzothiazole. 177 g of a water-moist paste are obtained, corresponding to 35.7 g of 6-nitrobenzothiazol-2-yl-formamide of melting point 262°-266° C. After recrystallising from a large amount of methylglycol acetate, the product has a melting point of 268°-269° C. The water-moist paste is suspended in 350 ml of methanol and saponification is carried out as in Example 1. After drying the product, 30.6 g of 6-nitro-2-aminobenzothiazole of melting point 248°-251° C. are obtained. The content of 5-isomer is less than 0.05% and the content of the 4- and 7-isomers is less than 1.2%. The crude product can be used, without further purification, for the preparation of dyestuffs.

EXAMPLE 6

178 g (1.0 mol) of 2-benzothiazolyl-formamide are nitrated as described in Example 1 for 2-acetylaminobenzothiazole. The nitration composition is then discharged onto 1,450 g of ice-water, so that the resulting sulphuric acid concentration is about 30%. The suspension of 2-(6-nitrobenzothiazolyl)-formamide is warmed to 60° C. and stirred at this temperature for 2 hours. After the reaction mixture has been cooled to 30° C., it is neutralised to a pH value of 5-6 by adding 1,420 ml of 25% strength sodium hydroxide solution and the 2-amino-6-nitrobenzothiazole is filtered off and washed with 3 liters of water in portions. After drying the product at 80° C. in a vacuum cabinet, a yield of 194 g with a melting point of 248°-250° C. is obtained. The 2-amino-6-nitrobenzothiazole obtained in this manner contains at most 1.5% each of the isomeric 4-, 5- and 7-nitro compounds and can be employed, without special purification, for the preparation of dyestuffs.

We claim:

1. A process for the preparation of 2-amino-6-nitro-benzothiazole comprising reacting an acylaminobenzthiazole of the formula

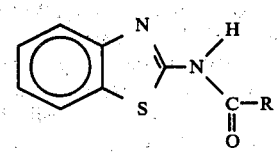

in which

R is hydrogen, $C_1$-$C_4$-alkyl or $C_1$-$C_4$-alkoxy, with nitric acid at a molar ratio of said acylaminobenzthiazole to nitric acid of 1:10 at a temperature of 0°-50° C. thereby to produce 6-nitro-2-acylamino-benzthiazole, and saponifying the 6-nitro-2-acylamino-benzthiazole with a dilute mineral acid, alkali hydroxide or ammonia at 20°-150° C.

2. The process according to claim 1, wherein the molar ratio of acylaminobenzthiazole to nitric acid is 1:2-10.

3. The process according to claim 1, wherein the nitric acid is mixed with sulphuric acid and the molar ratio of acylaminobenzthiazole to nitric acid is 1:1-1.5.

4. The process according to claim 1, wherein R is hydrogen or methyl.

* * * * *